United States Patent [19]
Seo et al.

[11] Patent Number: 5,062,427

[45] Date of Patent: Nov. 5, 1991

[54] ULTRASONIC DOPPLER APPARATUS

[75] Inventors: Yasutsugu Seo, Ootawara; Motoaki Sugawara, 10-14, Higashimine-machi, Oota-ku, Tokyo, both of Japan

[73] Assignees: Kabushiki Kaisha Toshiba, Kawasaki; Motoaki Sugawara, Tokyo, both of Japan

[21] Appl. No.: 424,337

[22] Filed: Oct. 19, 1989

[30] Foreign Application Priority Data

May 6, 1988 [JP] Japan .................................. 63-110171
Oct. 21, 1988 [JP] Japan .................................. 63-265518

[51] Int. Cl.$^5$ .............................................. A61B 8/06
[52] U.S. Cl. .............................. 128/661.10; 73/861.25
[58] Field of Search ..................... 128/661.07–661.10; 73/861.25

[56] References Cited

U.S. PATENT DOCUMENTS

| | | | |
|---|---|---|---|
| 4,408,349 | 10/1983 | Yukawa | 455/182 |
| 4,501,279 | 2/1985 | Seo | 128/661.1 |
| 4,660,565 | 4/1987 | Shirasaka | 128/661.09 |
| 4,790,322 | 12/1988 | Iinuma | 128/661.1 |
| 4,873,985 | 10/1989 | Nakajima | 128/661.1 X |

FOREIGN PATENT DOCUMENTS

86/05637 9/1986 PCT Int'l Appl. .

OTHER PUBLICATIONS

M. Sugawara et al., "A Feasible Method of Measuring the Absolute Flow-Rate of a Regurgitation, Shunt, and Stenosed Flow by Color Doppler", Journal of the International Organization for Medical Physics, Physics in Medicine & Biology, vol. 33, Supp. 1 (1988), 356.

*Primary Examiner*—Francis Jaworski
*Attorney, Agent, or Firm*—Finnegan, Henderson, Farabow, Garrett, and Dunner

[57] ABSTRACT

An input device for specifying a first measuring point near an orifice, for example, at the valve port position of the heart on a color Doppler image and a second measuring point on the centerline of an issuing fluid is connected to a blood flow imaging device which is a color Doppler tomograph constituted by combining a sector electronic scanning type ultrasonic diagnostic device and an Doppler system to derive blood flow information and tomographic image (B mode image) information by using a single ultrasonic probe. The blood flow imaging device derives Doppler shift frequencies at the first and second measuring points and supplies the same to a flow-rate calculating circuit. The flow-rate calculating circuit derives flow velocities of the blood at the first and second measuring points and a distance between the first and second measuring points and calculates the flow-rate based on the derived flow velocities and distance. The blood flow information and tomographic image obtained by the blood flow imaging device and the calculating result of the flow-rate calculating circuit are supplied to a display control circuit via a CPU bus and displayed on an display unit under the control of the display control circuit.

15 Claims, 12 Drawing Sheets

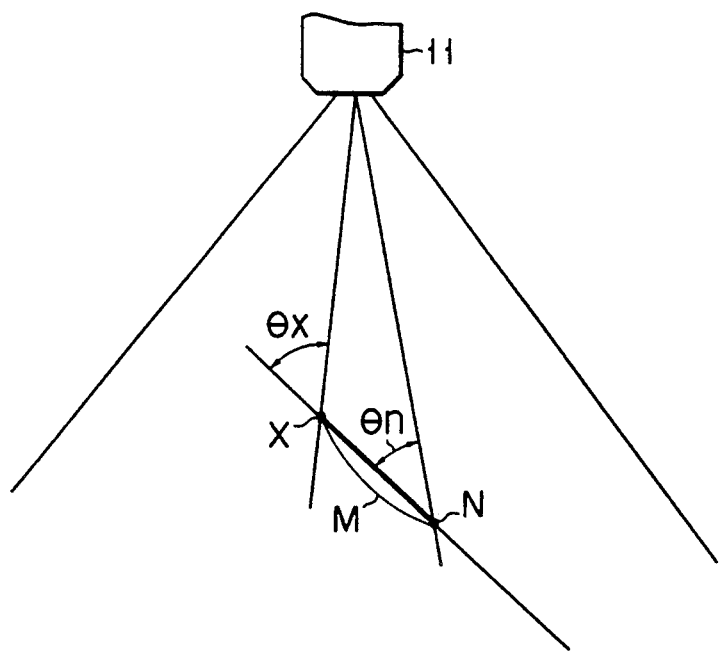
F I G. 5
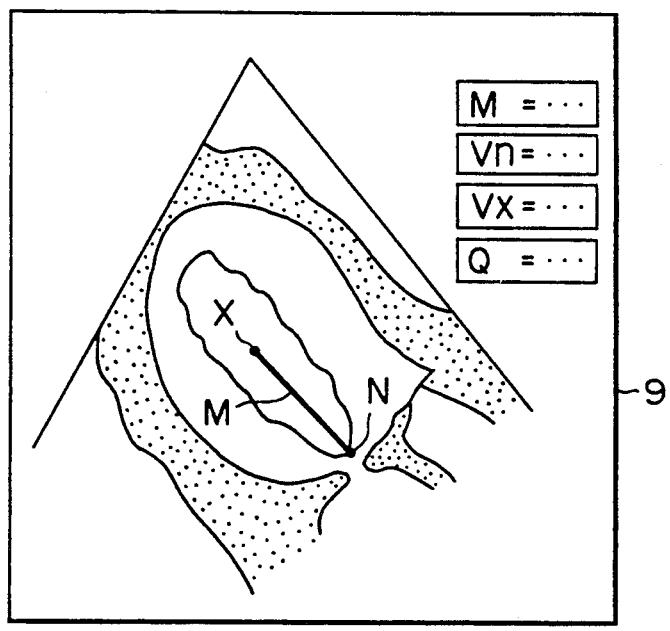
F I G. 6

ULTRASONIC DOPPLER APPARATUS

BACKGROUND OF THE INVENTION

1. Field of the Invention

This invention relates to an ultrasonic Doppler apparatus capable of measuring the flow-rate by utilizing the ultrasonic Doppler effect.

2. Description of the Related Art

It is expected that a color Doppler flow imaging system can be used to quantize the regurgitation flow in a noninvasive manner instead of the conventional X-ray cardiography. At present, however, no method for grading the severity of the regurgitation flow by use of the color Doppler method is presented. A method which has been presented is to effect the grading based not on the absolute flow-rate of the regurgitation flow jet but on the geometric characteristics such as the length, width and area of the regurgitation flow jet. The jet flowrate is obtained by flow velocity×cross-sectional area. However, it is extremely difficult to correctly measure the cross-sectional areas of the orifice of the regurgitation flow, such as valvular regurgitation flow, shunt flow and stenosed flow, by means of the Doppler method.

SUMMARY OF THE INVENTION

An object of this invention is to provide an ultrasonic Doppler apparatus capable of deriving the issuing flow-rate by use of the property of turbulent free jet without measuring the cross-sectional area of the orifice.

Another object of this invention is to provide an ultrasonic Doppler apparatus capable of correctly determining the issuing flow-rate in a brief period of time by measuring a distance and the flow-rate at one position.

An ultrasonic Doppler apparatus according to one aspect of this invention comprises a blood flow imaging device for transmitting ultrasonic waves to fluid issued from an orifice, receiving the reflected echo thereof and displaying a tomographic image of the fluid, an input device for specifying, on the tomographic image, a first point near the orifice and a second point lying on that part of the centerline of the issued fluid which lies on a portion other than the laminar core, a velocity calculating circuit for deriving the flow velocities at the first and second points, a distance calculating circuit for deriving a distance between the first and second points, and a flow-rate calculating circuit for deriving the issuing flow-rate of fluid based on the two velocities derived by means of the velocity calculating circuit and the distance derived by means of the distance calculating circuit.

An ultrasonic Doppler apparatus according to another aspect of this invention comprises a blood flow imaging device for transmitting ultrasonic waves to fluid issued from an orifice, receiving the reflected echo thereof and displaying a tomographic image of the fluid with a portion having a predetermined velocity distinguished from the remaining portion, an input device for specifying, on the tomographic image, a first point near the orifice and a second point lying on the centerline of the issued fluid which lies in the distinguished portion having the predetermined velocity, a velocity calculating circuit for deriving the flow velocity at the first point, a distance calculating circuit for deriving a distance between the first and second points, and a flow-rate calculating circuit for deriving the issuing flow-rate of fluid based on the predetermined velocity, the flow velocity derived by means of the velocity calculating circuit and the distance derived by means of the distance calculating circuit.

An ultrasonic Doppler apparatus according to a still another aspect of this invention comprises a blood flow imaging device for transmitting ultrasonic waves to fluid issued from an orifice, receiving the reflected echo thereof and displaying a tomographic image of the fluid, a velocity calculating circuit for deriving the flow velocity at the orifice, a distance calculating circuit for deriving a distance to a point on the centerline of a portion of the issued fluid which lies at the remotest position and has substantially the same velocity as that at the orifice, and a flow-rate calculating circuit for deriving the issuing flow-rate of the fluid based on the flow velocity derived by means of the velocity calculating circuit and the distance derived by means of the distance calculating circuit.

BRIEF DESCRIPTION OF THE DRAWINGS

FIG. 5 is a diagram for illustration of the principle of flow-rate calculation in the first embodiment;

FIG. 6 shows an example of an image obtained in the first embodiment;

DETAILED DESCRIPTION OF THE PREFERRED EMBODIMENTS

Figure 1:
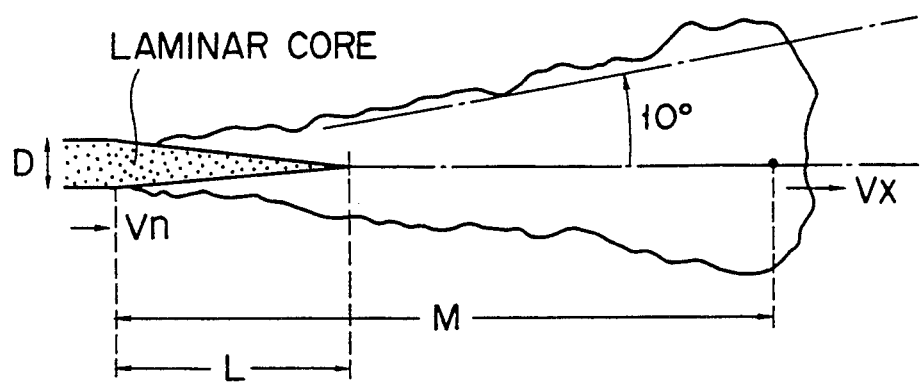
FIG. 1 is a view showing the turbulent free jet and illustrating the principle of this invention.

There will now be described an ultrasonic Doppler apparatus according to an embodiment of this invention with reference to the accompanying drawings. First, the principle of deriving the flow-rate in this invention is explained before explaining the construction of this embodiment. When the turbulent free jet is issued from an orifice at an issuing velocity Vn, a portion in which the issued fluid is still separated from the surrounding fluid lies in the central portion of the jet within the distance L from the orifice as shown in FIG. 1. This portion is called a laminar core. The flow velocity inside the laminar core is substantially kept at Vn. Assume that the cross section of the orifice is circular the diameter thereof is D, and the flow velocity at the center of a portion of the jet which is separated from the orifice by a distance M (M>L) is Vx. Then, it is known that the following relation can be obtained.

$$L = 6.8D \ldots \quad (1)$$

$$Vx/Vn = L/M \ldots \quad (2)$$

It is also known that the jet diverges in a conical shape with a half-apex angle of approx. 10°. The following equation can be obtained by substituting Eq. (1) into Eq. (2):

$$Vn \cdot D = (Vx/6.8) \cdot M \ldots \quad (3)$$

Suppose that Vx is set to the lowest possible velocity which can be measured by using an ultrasonic Doppler device and is independent from the angle. Then, M can be regarded as being a distance which the jet can travel in the device. At this time, since Vx is an inherent constant value of the device, Eq. (3) can be rewritten as follows:

$$Vn \cdot D \propto M \ldots \quad (4)$$

The relation expressed by Eq. (4) has been experimentally confirmed by Wranne et al. Since the left-hand term of Eq. (4), i.e., Vn·D is neither the flow-rate nor the size of the orifice, the flow-rate of the regurgitation flow or the size of the orifice cannot be graded based only on the traveling distance M of the jet. However, the following equation (5) which can be obtained by dividing Eq. (4) by Vn indicates that the traveling distance M divided by the issuing flow velocity Vn can be used as an index of the size of the orifice.

$$D \propto M/Vn \ldots \quad (5)$$

The issuing flow-rate Q of the jet can be given by $Q = (\pi D^2/4)Vn$. The following equation can be obtained by substituting Eq. (3) into the above equation:

$$Q = 0.017 \cdot Vx^2 \cdot M^2 / Vn \ldots \quad (6)$$

Assume that Vx is the lowest possible velocity which be measured by using the ultrasonic Doppler device and is constant. The jet diverges in a conical form with a preset half-apex angle (approx. 10°) and therefore the cross sectional area S of the jet obtained by the flow imaging system varies with $M^2$. As a result, Eq. (6) can be rewritten as follows:

$$Q \propto S/Vn \ldots \quad (7)$$

The relation of Eq. (7) indicates that the area S of the jet divided by the issuing velocity Vn can be used as an index of the grading of the flow-rate Q.

As described above, the flow-rate Q can be derived according to Eq. (6) if the issuing velocity Vn, a flow velocity Vx at a point separated from the orifice by a distance M (>L) and lying on the centerline of the jet except the laminar core and the distance M can be detected. In the first embodiment of this invention, the velocity Vn at the orifice, the velocity Vx at a point on the centerline and the distance M from the orifice to the above point are first detected and then the flow-rate Q is derived according to Eq. (6).

Figure 2:
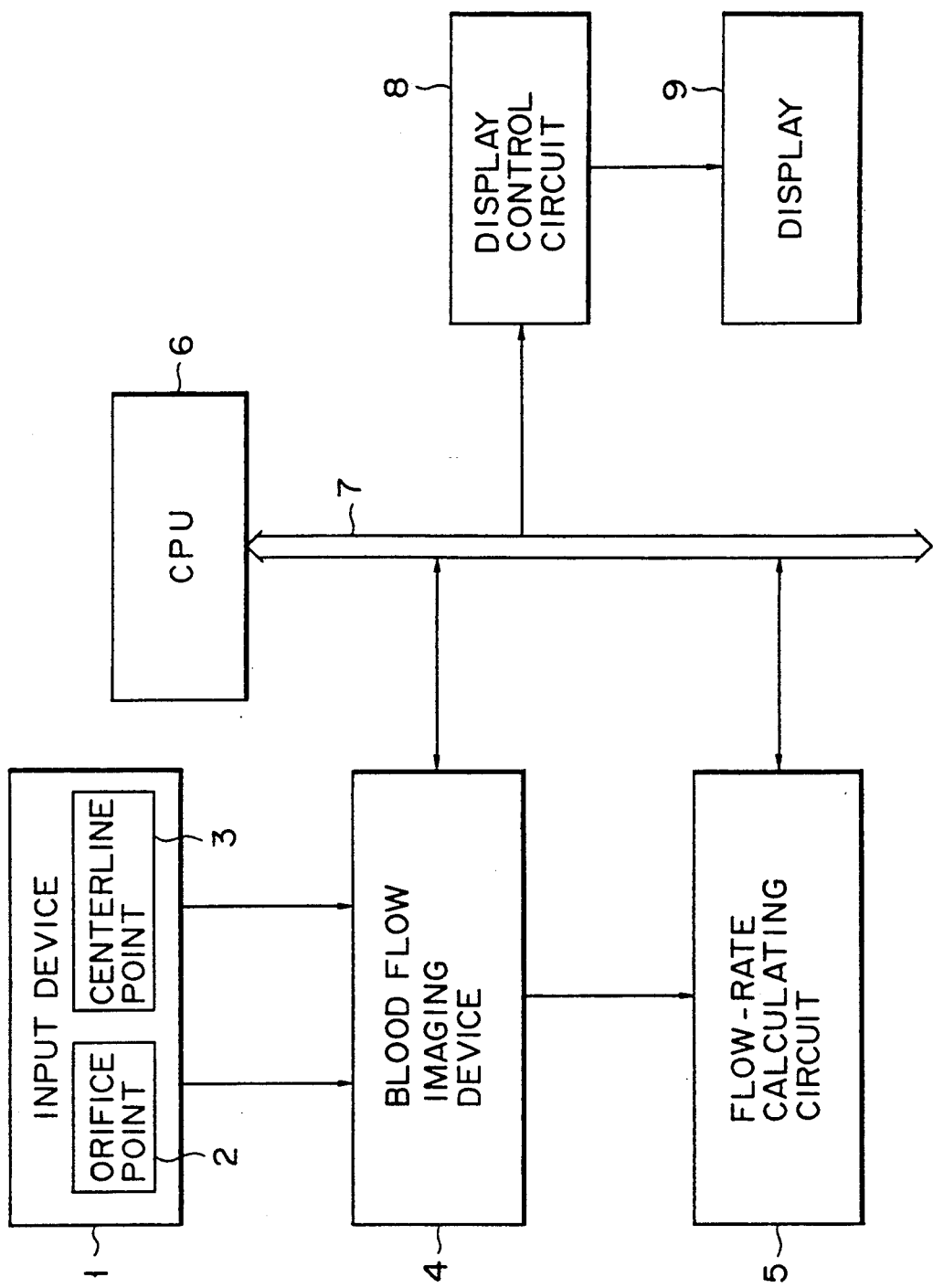
FIG. 2 is a block diagram of an ultrasonic Doppler apparatus according to a first embodiment of this invention.

FIG. 2 is a block diagram showing the construction of the first embodiment. An input device 1 includes a specifying unit 2 for specifying a point near the orifice as a first velocity measuring point, for example, a point N at the heart valve port position on a color Doppler image and a second specifying unit 3 for specifying a point X as a second velocity measuring point on the centerline of a portion of the issuing fluid other than the laminar core. For example, a track ball or the like provided on the operation panel can be used as the first and second measuring point specifying units 2 and 3. A signal generated from the input device 1 and indicating the positions of the first and second measuring points is supplied to a blood flow imaging device 4.

The blood flow imaging device 4 is a color Doppler tomography device having a combination of a sector electronic scanning type ultrasonic diagnostic device and a ultrasonic Doppler device. The blood flow imaging device 4 can provide blood flow information and tomographic image (B mode image) information by use of a single ultrasonic probe, and will be explained in detail with reference to FIG. 3. A signal from the blood flow imaging device 4 is supplied to a flow-rate calculating circuit 5. The flow-rate calculating circuit 5 calculates the flow velocity and the flow-rate of blood, and will be described in detail with reference to FIG. 4. The blood flow imaging device 4 and the flow-rate calculation circuit 5 are connected to a CPU bus 7.

The blood flow information derived by the blood flow imaging device 4 and the calculation result of the flow-rate calculating circuit 5 are transferred to a display control circuit 8 via the CPU bus 7 and displayed on a display unit 9 under a control of the display control circuit 8. A CRT display is used in the display unit 9. A central processing unit (CPU) 6 functions to control the operation of the whole apparatus of this embodiment.

Figure 3:
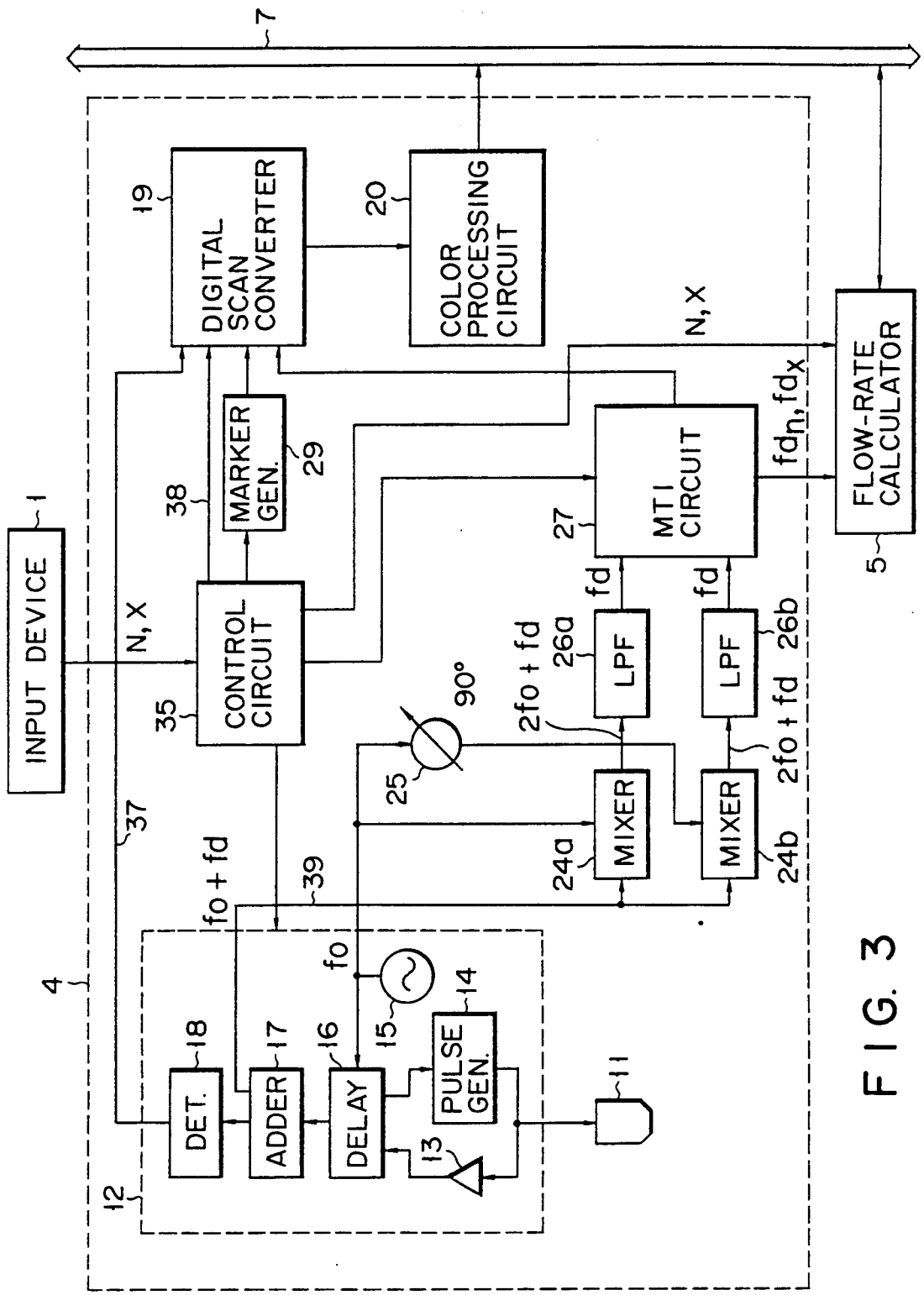
FIG. 3 is a circuit diagram of a blood flow imaging device used in the first embodiment.

Next, the detail construction of the blood flow imaging device 4 is explained with reference to FIG. 3. An ultrasonic probe 11 including a number of piezoelectric elements arranged in an array fashion to transmit or receive ultrasonic waves to or from an object is connected to a sector electronic scanning unit 12. The sector electronic scanning unit 12 is constructed by a preamplifier 13, a pulse generator 14, an oscillator 15, a delay line 16, an adder 17 and a detector 18. An output of the detector 18 is supplied to a digital scan converter 19 and converted into lattice-form scanning line data by interpolating data between scanning lines of the sector-form scanning line data. An output of the digital scan converter 19 is supplied to the CPU bus 7 via a color processing circuit 20. A signal from a control circuit 35 connected to the input device 1 and the CPU bus 7 is supplied to the digital scan converter 19 via a marker generator 29.

One of the two signals from the adder 17 is supplied to the digital scan converter 19 via the detector 18 and a line 37 and is used to display a tomographic image (monochrome B mode image). The other signal from the adder 17 is supplied to line 39 and used to display a blood flow image. The signal on the line 39 is divided into two components which are respectively supplied to mixers 24a and 24b. A reference signal fo from the oscillator 15 is supplied to the mixer 24a and supplied to the mixer 24b after the phase thereof is shifted by 90° by means of a 90° phase shifter 25. As a result, a Doppler shift frequency component fd and a signal (2fo+fd) are respectively supplied to low-pass filters 26a and 26b, the high frequency components thereof are removed by the low-pass filters 26a and 26b and only the Doppler shift frequency components fd are obtained. The Doppler shift frequency components fd are used as phase-detected output signals for formation of a blood flow distribution image and calculation of flow velocities Vn and Vx. Mixers of two channels are used to determine the direction of movement of the blood flow, or whether fd is positive or negative.

The phase-detected output signal includes not only the blood flow information but also an unwanted reflected signal (called clutter) from an object such as the wall of the heart whose movement is slow. In order to remove the clutter, the phase-detected output signal is supplied to a moving target indicator (MTI) circuit 27. The MTI circuit 27 includes A/D converters, plural line memories, MTI filters, an autocorrelation unit, an average velocity calculation unit, a distribution calculation unit and a power calculation unit. Outputs of the low-pass filters 26a and 26b are supplied to the autocorrelation unit via the A/D converters and the MTI filters. The MTI filter is constructed by a delay line and a subtracter and functions to cancel signal components from an object whose movement is slow by subtracting two reflected waves taken at a preset time interval from each other. The autocorrelation unit analyzes the frequency of the signal from which the clutter is removed. An output of the autocorrelation unit is supplied to the average velocity calculating unit and distribution calculation unit. The distribution of the Doppler shift frequency and the average Doppler shift frequency fd calculated for each point are input to the digital scan converter 19, subjected to a data interpolation process and then converted into color information by means of the color processing circuit 20. For example, it is a common practice to display the fluid approaching the probe 11 in red-series color and the fluid departing from the probe in blue-series color and represent the average velocity by the brightness of the color and the velocity distribution by hue (mixed with green). In general, the high-speed blood flow has a large velocity distribution value, the approaching fluid is displayed in bright orange-color and the departing fluid is displayed in blue-green.

The marker generator 29 generates information for forming markers indicated in the positions of the measurement points N and X specified by the first and second measuring point specifying units 2 and 3 of the input device 1. The marker forming information is superimposed on the color Doppler image by the digital scan converter 19. The position information of the first and second measuring points is supplied to the flow-rate calculating circuit 5 via the control circuit 35.

Figure 4:
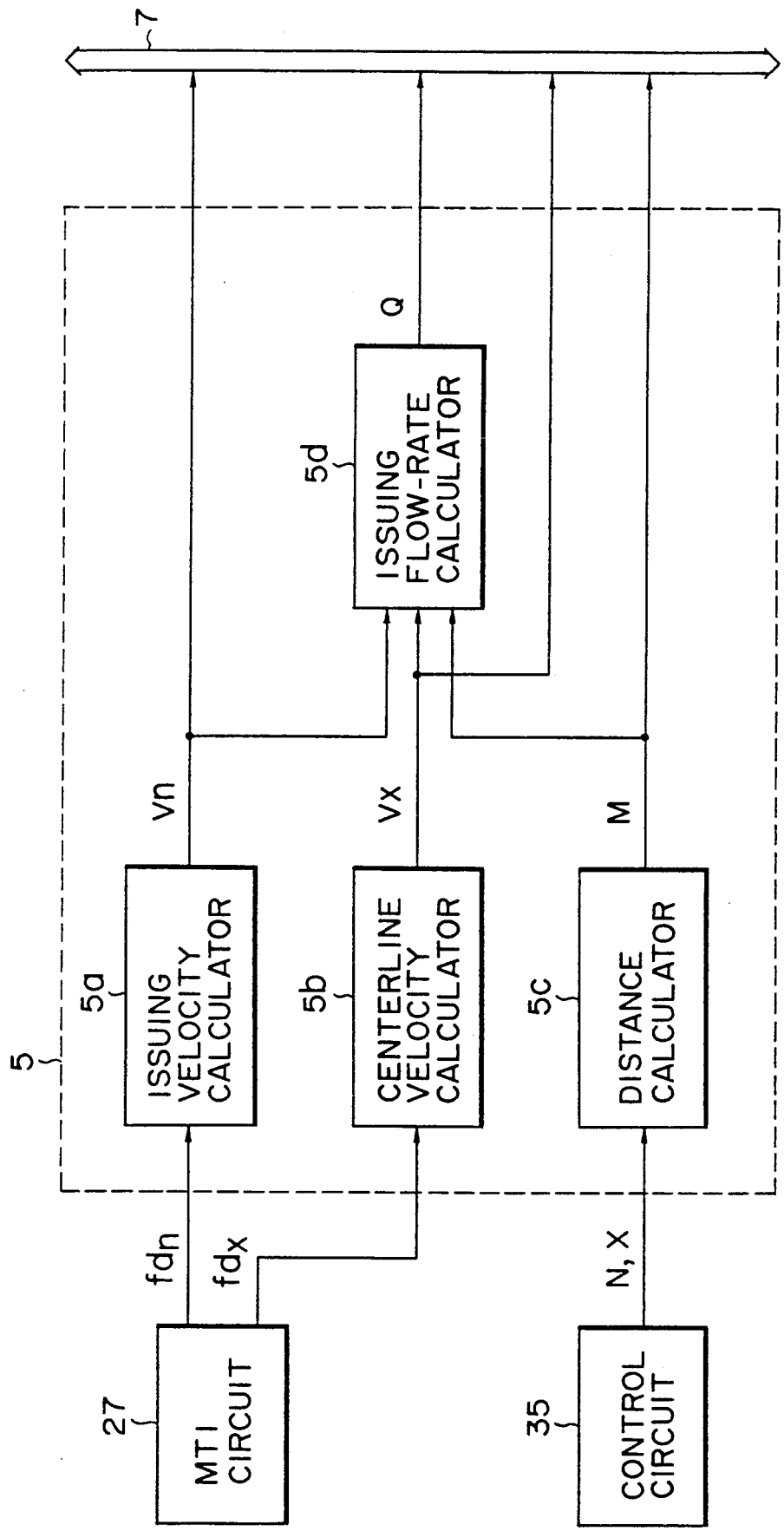
FIG. 4 is a circuit diagram of a flow-rate calculating circuit used in the first embodiment.

Next, the flow-rate calculating circuit 5 is explained in detail with reference to FIG. 4. The flow-calculating circuit 5 is functionally constructed by an issuing velocity calculator 5a, a centerline velocity calculator 5b, a distance calculator 5c and a flow-rate calculator 5d. The issuing velocity calculator 5a derives the flow velocity Vn of blood at the first measuring point N set near the orifice by the first measuring point specifying unit 2. The centerline velocity calculator 5b derives the flow velocity Vx of blood at the measuring point X set on the centerline by the second measuring point specifying unit 3. The distance calculator 5c derives a distance M between the first and second measuring points. Further, the flow-rate calculator 5d calculates an issuing flow-rate Q of blood based on the calculation results of the calculators 5a, 5b and 5c. The calculation of the issuing flow-rate Q is made based on Eq. (6).

Now, the algorithm of the velocity calculators 5a and 5b is explained. In FIG. 5, the scanning lines from the ultrasonic probe 11 are shown. The B mode image and blood flow distribution image of an object (in this example, a heart) are formed based on the received echo of the ultrasonic waves transmitted from the probe 11. The blood flow distribution image (color image) is superimposed on the B mode image (monochrome image) and displayed. The displayed image is the color Doppler image. When the first measuring point N is set on the color Doppler image, the velocity calculator 5a calculates the flow velocity Vn at the first measuring point N according to Eq. (8).

$$Vn = fd_n \cdot C/(2fo \cdot \cos\theta n) \ldots \quad (8)$$

When the second measuring point X is set on the color Doppler image, the velocity calculator 5b calculates the velocity Vx at the second measuring point X according to Eq. (9).

$$Vx = fd_x \cdot C/(2fo \cdot \cos\theta x) \ldots \quad (9)$$

In Eqs. (8) and (9), $fd_n$ and $fd_x$ are Doppler shift frequencies at the points N and X, C is a propagation velocity (sound velocity) of ultrasonic waves in the living body, fo is the center frequency (the oscillation frequency of the oscillator 15) of the ultrasonic waves. Further, $\theta x$ and $\theta n$ are angles made by the centerline of the issued fluid and the scanning lines radially extending in a sector form with the ultrasonic probe 11 as the center and passing the points N and X, as shown in FIG. 5. The distance M between the first and second measuring points is derived based on the coordinate information of the first and second measuring points N and X.

Next, the operation of the first embodiment constructed a described above is explained. The ultrasonic waves are transmitted and received by means of the sector electronic scanning unit 12 under the control of the control circuit 35 of FIG. 3, and the B mode image and blood flow distribution image of the object are formed and displayed on the display unit 9 under the control of the display control unit 8 of FIG. 2. FIG. 6 shows an example of the image.

An operator operates the input device 1 so as to specify the first and second measuring points N and X on the displayed image (color Doppler image). Then, in the flow-rate calculating circuit 5 of FIG. 4, Eq. (8) is calculated by means of the velocity calculator 5a to derive the flow velocity Vn at the first measuring point N and Eq. (9) is calculated by means of the velocity calculator 5b to derive the flow velocity Vx at the second measuring point X. Further, the distance M between the first and second measuring points is derived by the distance calculator 5c by use of the distance marker. In addition, Eq. (6) is calculated based on the calculation results of the calculators 5a, 5b and 5c by means of the flow-rate calculator 5d so as to derive the issuing flow-rate Q of blood at the first measuring point N or the issuing flow-rate of blood passing the orifice. The numeral data of the thus derived M, Vn, Vx and Q are displayed on the display screen of the display unit 9 under the control of the display control unit 8 as shown in FIG. 6.

As described above, according to the first embodiment, the issuing flow-rate of blood can be derived by setting the ultrasonic probe 11 towards the living body without measuring the cross-sectional areas of the orifice of the valvular regurgitation flow, shunt flow and stenosed flow, thus making it possible to grade the severity of the regurgitation flow based on the absolute flow-rate.

Now, the second embodiment of this invention is explained. In the first embodiment, the two measuring points are first specified and the velocities at the specified points are calculated. However, since the flow of the fluid at and near the second measuring point diverges, it is considered difficult to measure the flow velocity at a high precision. Therefore, in the second embodiment, a desired velocity is first specified, a portion corresponding to the specified velocity is displayed so as to be distinguished from the remaining portion on the color Doppler image (flow imaging), and then a point on the centerline of the portion corresponding to the specified velocity or a mean position of the point on the displayed portion when the displayed portion is moving is specified as the second measuring point. Therefore, the calculation for deriving the flow velocity at the second measuring point in the first embodiment can be omitted. The operation of deriving the flow-rate Q based on Vn, Vx and M is effected according to Eq. (6) in the same manner as in the first embodiment.

Figure 7:
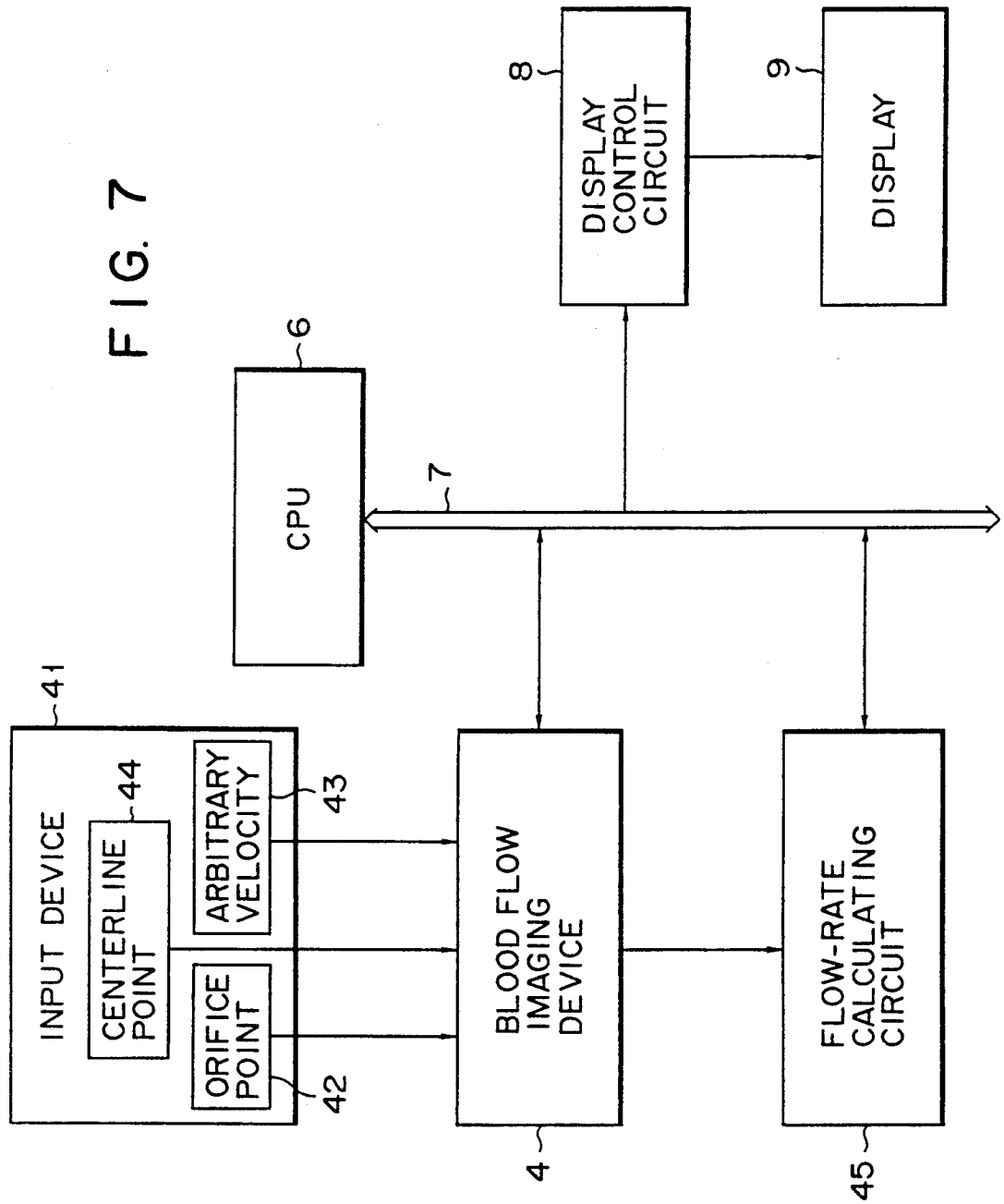
FIG. 7 is a block diagram of an ultrasonic Doppler apparatus according to a second embodiment of this invention.

FIG. 7 is a block diagram of the second embodiment. In the drawings, portions which have substantially the same functions as those used in the first embodiment are denoted by the same reference numerals as used in the first embodiment. The main difference between the second embodiment and the first embodiment lies in the constructions of an input device 41 and a flow-rate calculating circuit 45. The input device 41 includes a first specifying unit 42 for specifying a first measuring point near the orifice, a velocity specifying unit 43 for specifying an arbitrary velocity and a second specifying unit 44 for specifying a second measuring point on the centerline of a portion at the specified velocity. The measuring point specifying units 42 and 44 function to specify the first measuring point N on the orifice position (for example, the valve port of the heart) of the color Doppler image and the second measuring point X on the centerline. For this purpose, a track ball or the like is used in the same manner as in the first embodiment. A keyboard or the like is used in the velocity specifying unit 43.

Figure 8:
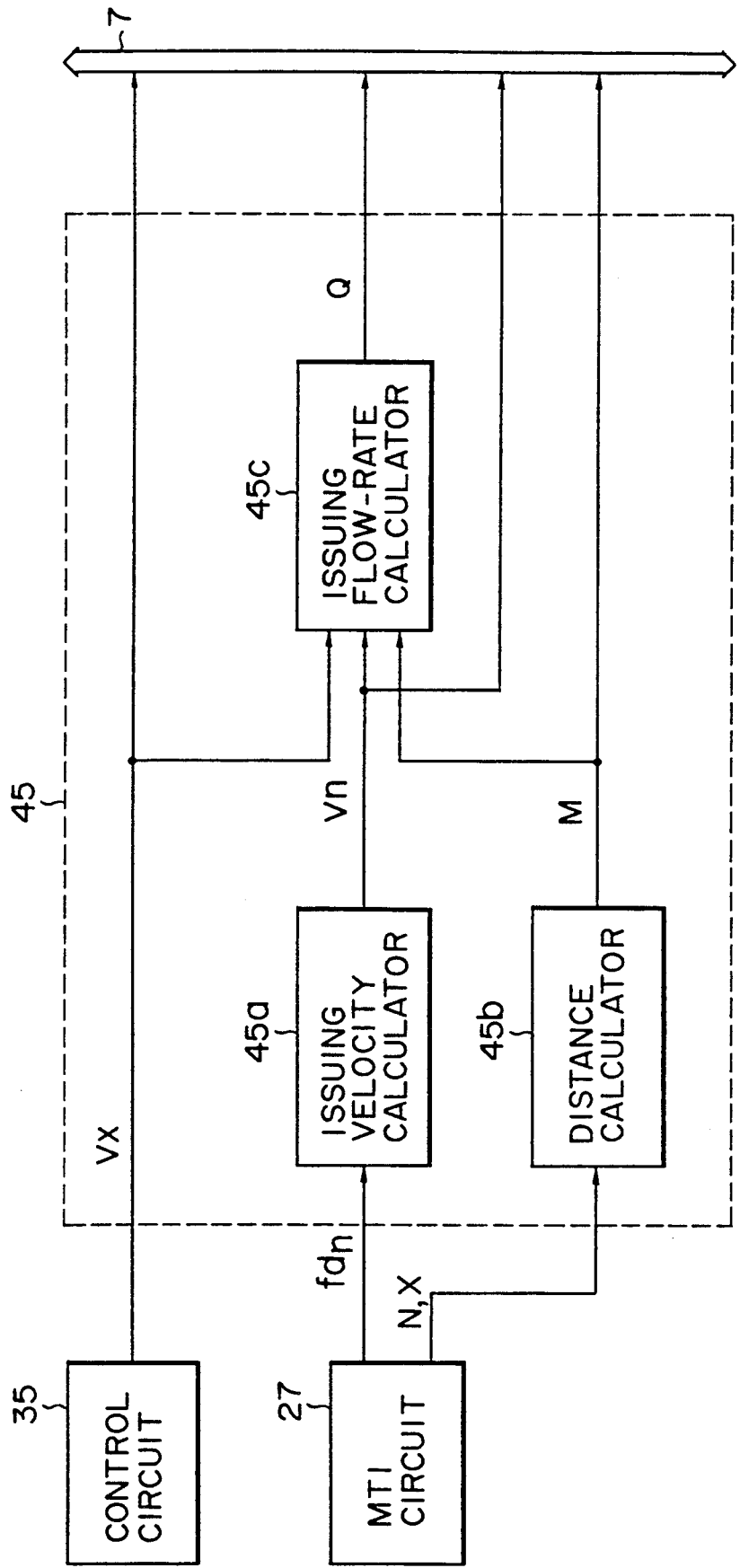
FIG. 8 is a circuit diagram of a flow-rate calculating circuit used in the second embodiment.

As shown in FIG. 8, the flow-rate calculating circuit 45 is functionally constructed by an issuing velocity calculator 45a, a distance calculator 45b and an issuing flow-rate calculator 45c. Like the velocity calculator 5a in the first embodiment, the velocity calculator 45a derives the issuing velocity Vn of blood at the measuring point N set by the measuring point specifying unit 42 according to Eq. (8). The distance calculator 45b derives a distance between the first measuring point N set near the orifice and a position corresponding to the flow velocity information specified by the velocity specifying unit 43 and lying on the velocity distribution (or the color Doppler image) or a mean position thereof.

Since the blood flow at the second measuring point X diverges, the measuring precision of the flow velocity Vx in the first embodiment will be degraded. However, in the second embodiment, the flow-rate measuring precision is enhanced by first setting the flow velocity Vx at a position corresponding to the second measuring point X and then detecting the distance M as described above.

Figure 9:
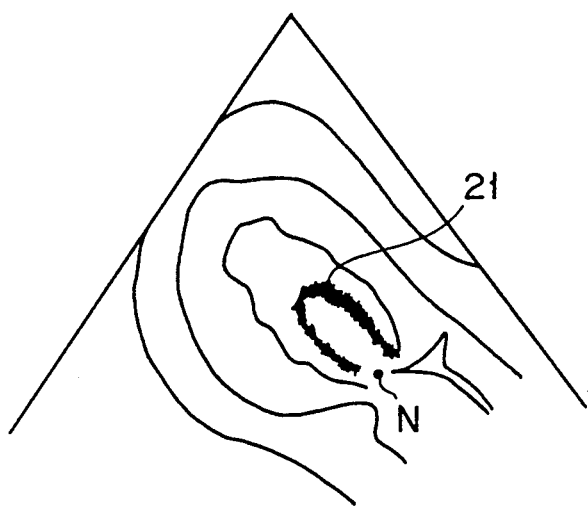
FIG. 9 is a diagram for illustrating the operation of the second embodiment.

As shown in FIG. 9, the blood flow imaging device 4 displays the specified velocity area 21 on the color Doppler image so as to be clearly distinguished from the remaining area. For example, a color different from that of the remaining area may be used for the area of the specified velocity. Since, in this example, the corresponding portion 21 moves, the distance M ca be measured by observing the displayed image if a specified color is used for the moving portion. The flow-rate calculator 45c receives the data Vx, Vn and M and derives the issuing flow-rate Q according to Eq. (6). In this case, Vx, Vn, M and the like may be displayed in the same manner as in the first embodiment shown in FIG. 4.

Figure 10:
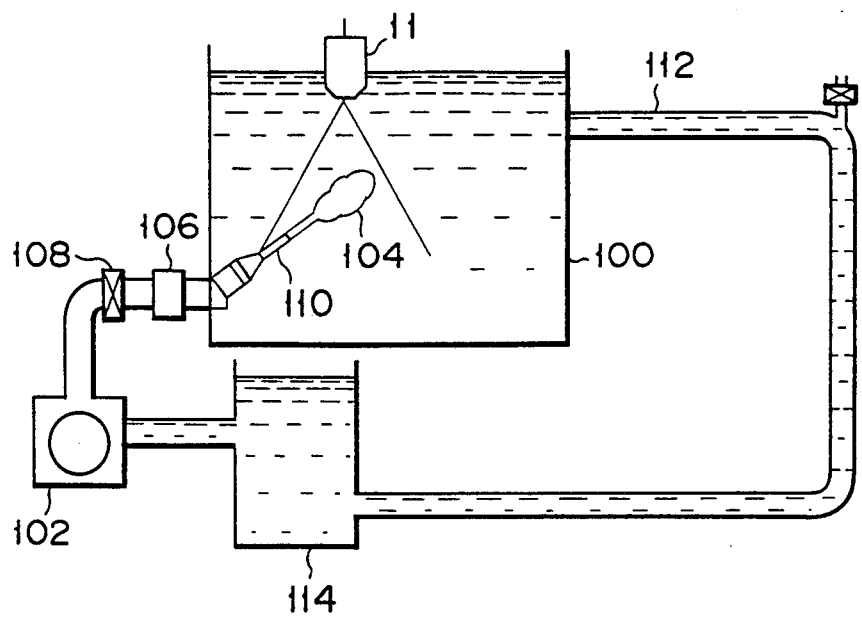
FIG. 10 is a block diagram of an experimental setup for evaluating the estimated flow-rate derived in the second embodiment.

Now, the experiment effected for comparing derived values (estimated values) according to the second embodiment with actually measured values is explained. FIG. 10 is a block diagram of a setup used for the experiment. A pulsative jet 104 is formed in a phantom device (water bath) 100 by a pulsation pump 102 and an ultrasonic probe 11 is disposed in the bath. A pulsation pump (model 1421) manufactured by Harvard Apparatus Co. was used as the pulsation pump 102. The pulsative displacement in each cycle was varied within a range of 5 to 30 ml, the pulsation frequency was set at 60/min, and the activation period was set at 35% of one pulsation period (in this case, the stationary period is 65% thereof) and at 65% of one pulsation period (in this case, the stationary period is 35% thereof). An aqueous solution of glycerin (50% in weight percentage, 28° C., coefficient of viscosity: 4.5 cp) was used as the fluid. Further, a hybrid CW probe (2.5 MHz) capable of detecting high velocity was used as the ultrasonic probe 11. The actual measurements of the flow-rate was obtained by means of an ultrasonic flow meter (which is operated to derive the flow-rate based on a difference between arrival times of the ultrasonic waves from two points set on both sides of the fluid and which has the measurement precision of 2%) 106 manufactured by Transonic System Co. In this case, Vn, Vx and M were measured while a valve 108 was adjusted to change the flow-rate within a range of 0.2 to 2.2 l/min. Since, at this time, the measurement stability of Vx was low, the measurement was made by use of color inversion (aliasing) using the zero-shift function. Since an error becomes large when an angle between the ultrasonic beam and the jet is set to be larger than 70°, the angle was set to be smaller than 60°. Further, nozzles with four different internal diameters of 1.4, 2.0, 3.0 and 4.0 mm were used as a nozzle 110. In FIG. 10, 112 denotes a silicone tube and 114 denotes a reservoir.

Figure 11:
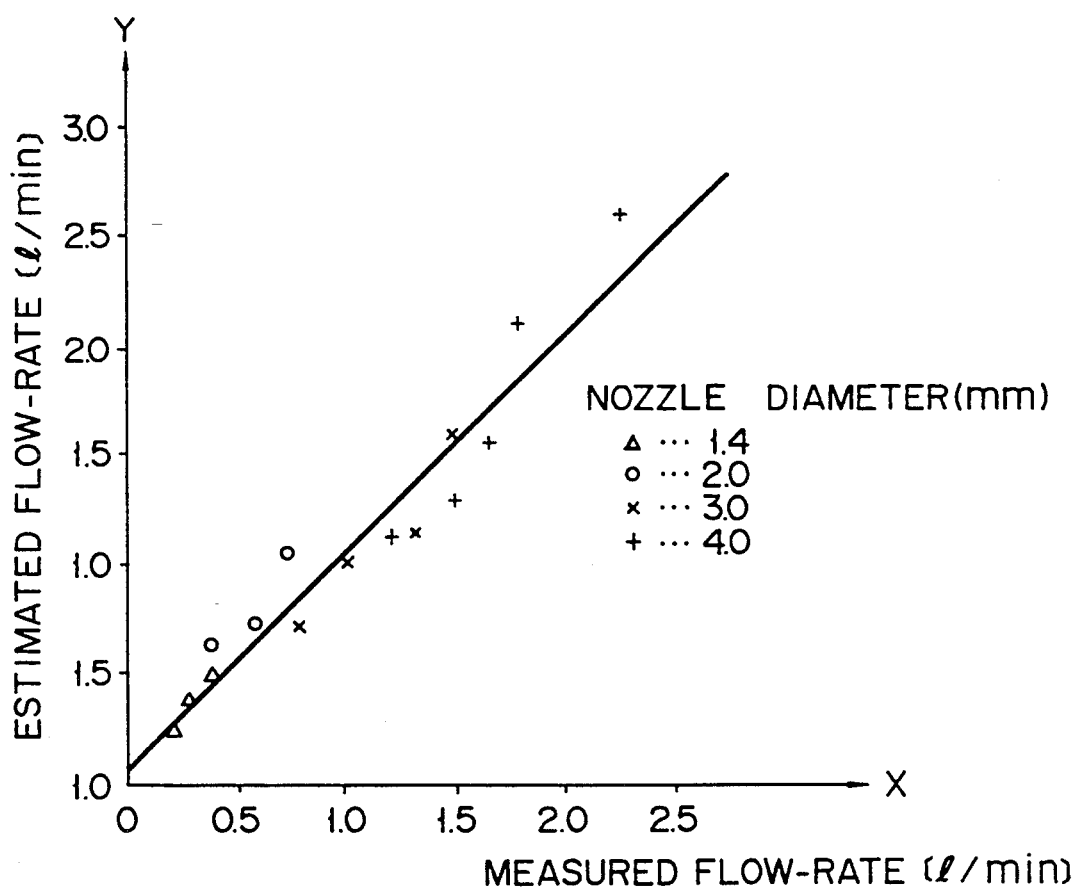
FIG. 11 is a graph showing estimated flow-rates obtained in the second embodiment in comparison with measured flow-rates derived by use of the experimental setup of FIG. 10.

FIG. 11 shows the relation between the estimated values of the flow-rate derived by using measured values of Vn. Vx and M in Eq. (6) and the flow-rates actually measured by the flow meter 106. A preferable relation can be obtained between the estimated values and the actually measured values as shown by the following equation:

$$Y = 1.01X + 0.06 \quad (r = 0.96, SE = 0.19).$$

It is clear from the result of the experiment that the jet flow-rate can be derived at a relatively high precision according to Eq. (6) in the case of turbulent free jet even if the cross sectional area of the orifice is not known. In order to obtain the turbulent free jet, it is necessary to use ray-nozzles of more than approx. 2500. In the case of the regurgitation flow in the left ventricle portion of the heart, since the pressure difference is approx. 80 mmHg and therefore the flow velocity becomes as high as 4 m/s, the above conditions may be satisfied in most cases.

Now, the third embodiment is explained. In the above-described embodiments, it is necessary to derive three data corresponding to the velocity at the first measuring point, the flow velocity at the second measuring point and the distance between the first and second measuring points and then calculate the issuing flowrate, thereby taking a long time for the calculation. In general, the flow velocity Vn of fluid such as blood issued from the orifice is substantially kept at the same value within a distance L from the orifice. Therefore, it is preferable to previously derive the flow velocity Vn and the distance L and then calculate the issuing flow-rate of fluid based on the two derived data. Since, in this case, the number of items of data to be previously derived is reduced, the measurement can be made in a shorter period of time.

In detail, when the turbulent free jet which is the blood flow from the valve port of the heart is issued from the orifice at the flow velocity Vn, the laminar core in which the issued blood is kept separated from the surrounding fluid remains in the central portion of the jet within a range of the distance L from the orifice as shown in FIG. 1. The flow velocity is kept at approx. Vn inside the laminar core. In order to measure the distance L which is the length of the laminar core, the following relation is assumed:

$$V1 = Vn \cdot (1-\alpha) \ldots \quad (10)$$

where $\alpha$ is a coefficient (set at 0.1, for example). Assuming that the cross section of the orifice is circular and the diameter is D, then the following equation is obtained:

$$L = 6.8D \ldots \quad (11)$$

Figure 14:
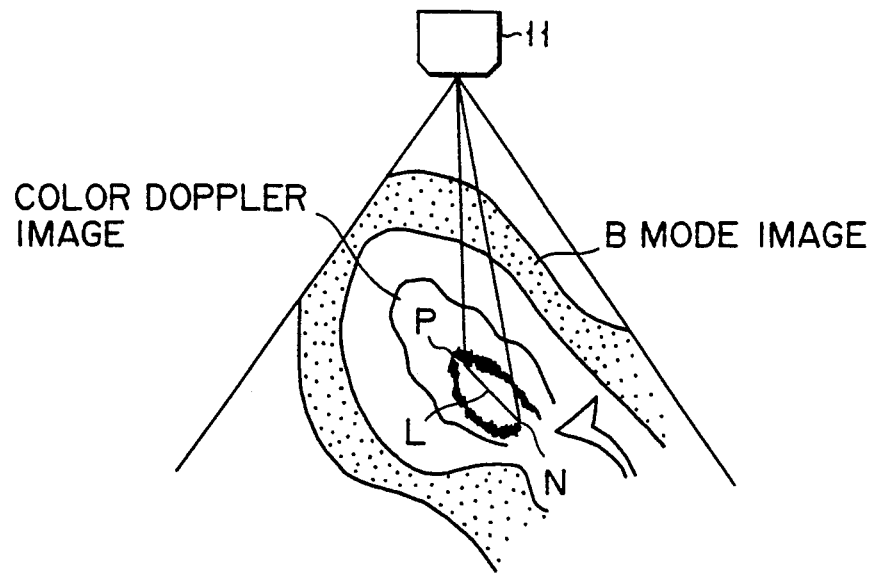
FIG. 14 is a diagram for illustrating the operation of the third embodiment.

A method for measuring L which satisfies Eq. (10) can be effected by displaying an area indicating the velocity higher than V1 in a specified color on the displayed color Doppler image and using a color marker to measure the distance between the specified color area and the orifice. Another method can be obtained by gradually moving the measurement sampling position P in an issuing direction from the orifice as indicated by an arrow as shown in FIG. 14 and setting the same at a position corresponding to V1.

Figure 12:
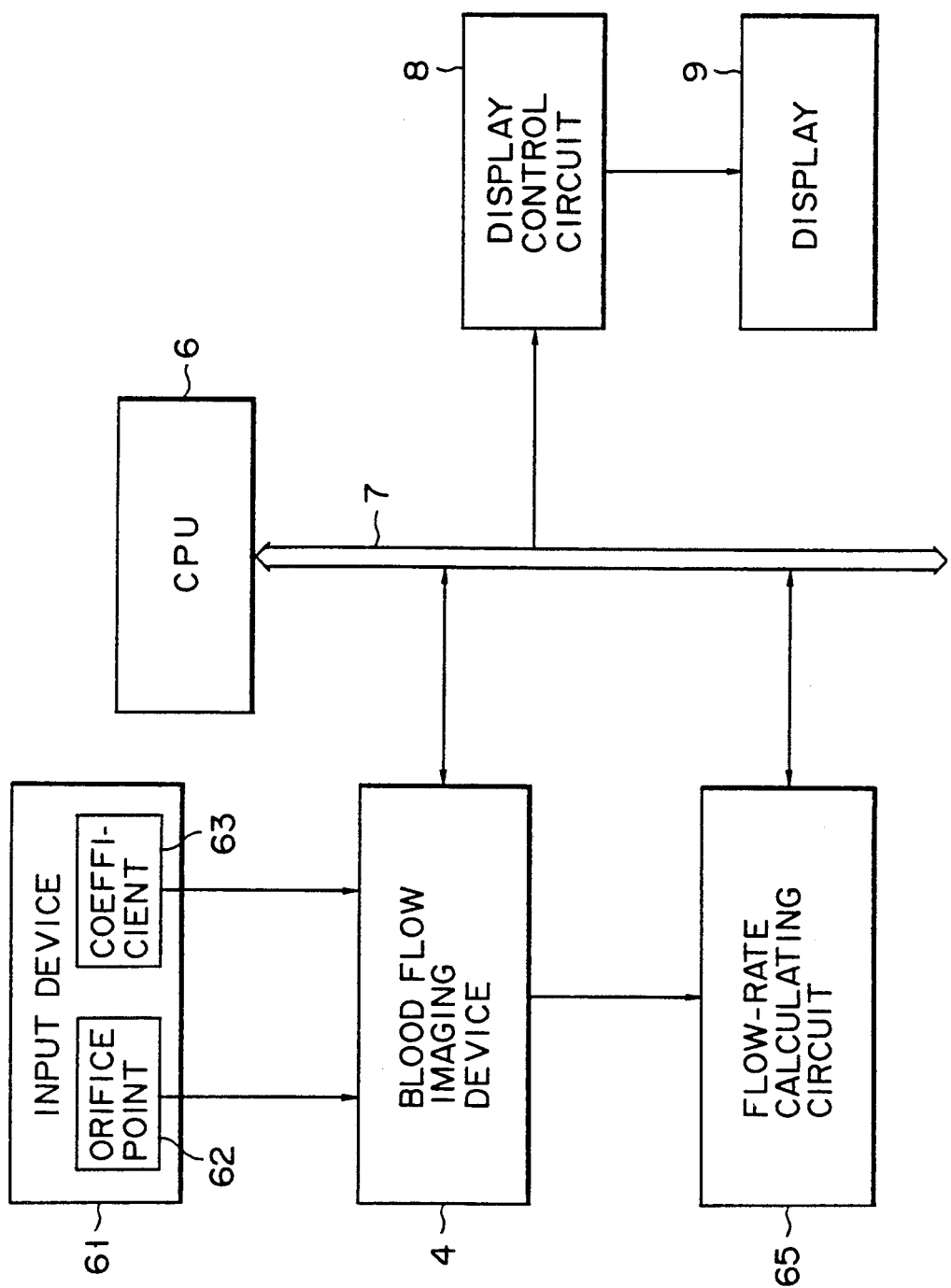
FIG. 12 is a block diagram of an ultrasonic Doppler apparatus according to a third embodiment of this invention.
Figure 13:
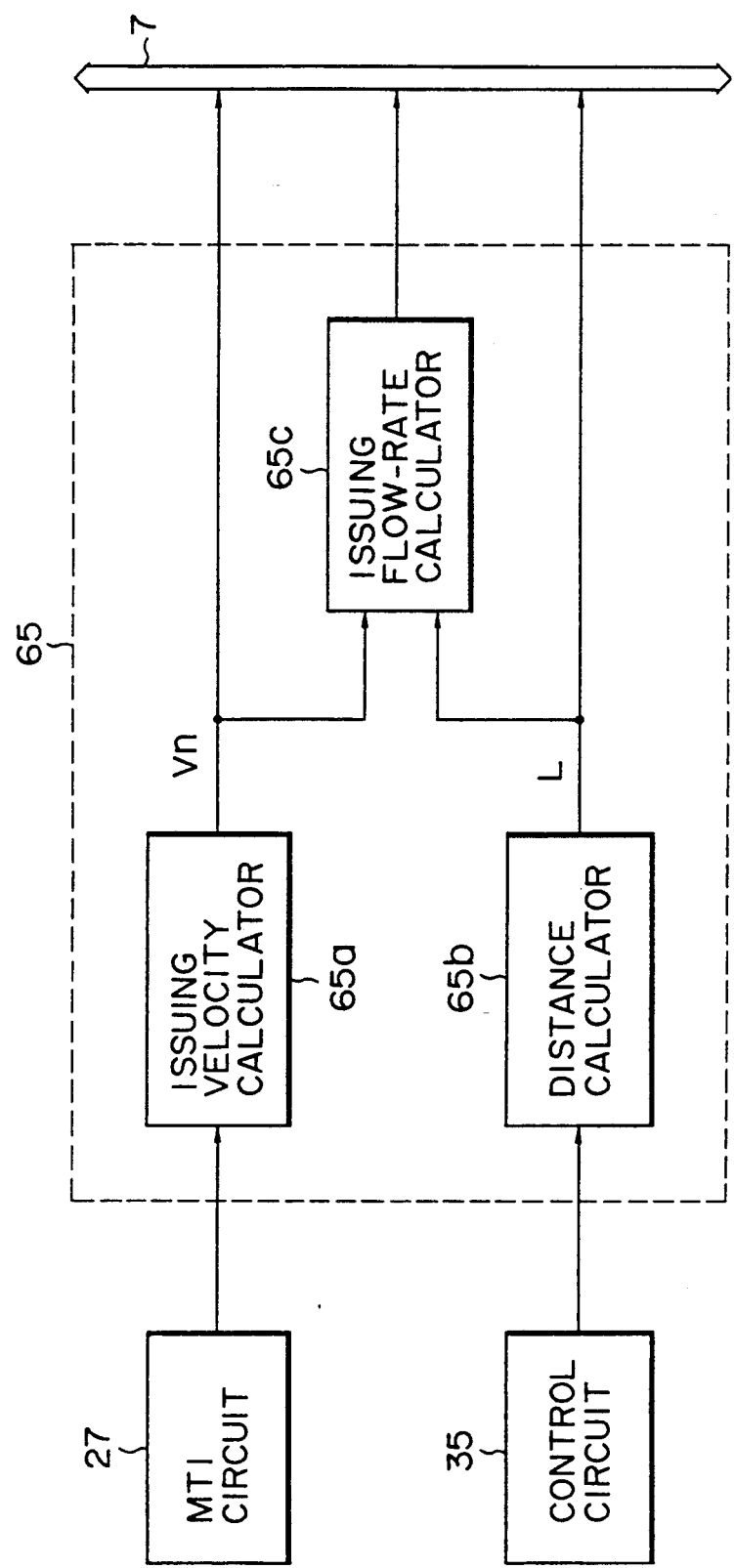
FIG. 13 is a circuit diagram of a flow-rate calculating circuit used in the third embodiment.

FIG. 12 is a block diagram of the third embodiment. The main difference between the third embodiment and the first embodiment lies in the constructions of an input device 61 and an issuing flow-rate calculating circuit 65. The input device 61 includes a measuring point specifying unit 62 and a coefficient ($\alpha$) specifying unit 63. The measuring point specifying unit 62 is constructed by a track ball or the like to set a measuring point N in a position of the orifice (the valve port of the heart, for example) on the color Doppler image displayed on a display unit 9. The coefficient specifying unit 63 sets the coefficient $\alpha$ used in Eq. (10) and may set 0.1 as the coefficient, for example. A track ball, mouse and the like arranged on the operation panel (not shown) may be used as the measuring point specifying unit 62 and the coefficient specifying unit 63.

The issuing flow-rate calculating circuit 65 is used to derive the flow velocity and the issuing flowrate of blood and is constructed to include an issuing velocity calculator 65a, a distance calculator 65b and issuing flow-rate calculator 65c. The velocity calculator 65a derives the flow velocity Vn of blood flow at a measuring point N set by the measuring point specifying unit 62 according to Eq. (8). The distance calculator 65b causes an area corresponding to the velocity of higher than V1 to be displayed in a specified color on the color Doppler image and measures the distance L between the orifice and the color area by using a distance marker. The issuing flow-rate calculator 65c derives the issuing flow-rate Q of blood based on data Vn and L derived by the calculators 65a and 65b. The issuing flow-rate Q can be derived according to the following equation:

$$\begin{aligned} Q &= \pi \cdot (D/2)^2 \cdot Vn \\ &= \pi \cdot \{(L/6.8)/2\}^2 \cdot Vn \\ &= 0.017 \cdot L^2 \cdot Vn \end{aligned} \quad (12)$$

Now, the operation of the third embodiment is explained. The ultrasonic waves are transmitted and received by means of the sector electronic scanning unit 12 under the control of the control circuit 35 in the blood flow imaging circuit 4, and the B mode image and blood flow distribution image of an object are formed and displayed on the display unit 9 under the control of the display control unit 8.

Figure 15:
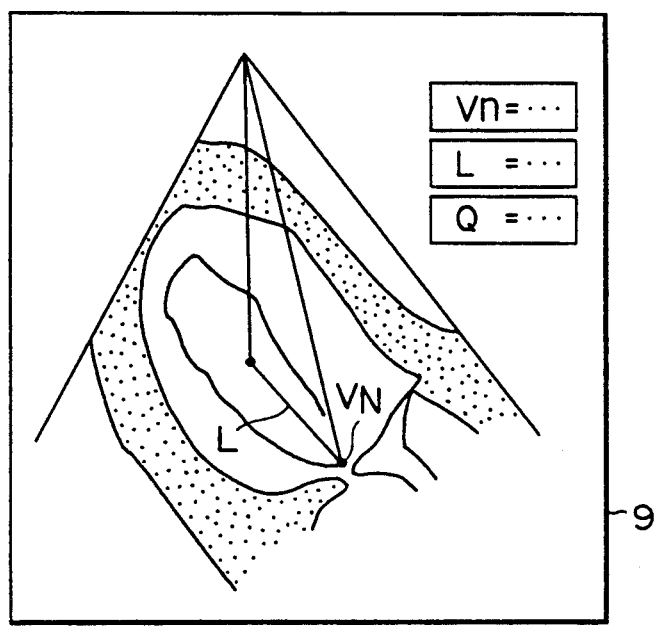
FIG. 15 shows an example of an image obtained in the third embodiment.

An operator operates the input device 1 to set the coefficient $\alpha$ and the measuring point N on the displayed image (color Doppler image). Then, the flow velocity Vn is derived based on the thus set measuring point and coefficient according to Eq. (8) by means of the velocity calculator 65a and at the same time the distance L which satisfies Eq. (10) is derived by the distance calculator 65b. Then, the thus derived data Vn and L are input to the flow-rate calculator 65c and the flow-rate at the measuring point N or the issuing flow-rate Q is derived according to Eq. (12). The numeral data of the thus derived flow velocity Vn, distance L and issuing flow-rate Q are displayed on the display screen of the display unit 9 under the control of the display control unit 8 as shown in FIG. 15.

According to the third embodiment, the issuing flow-rate of blood can be derived without measuring the cross-sectional areas of the orifice of the valvular regurgitation flow, shunt flow and stenosed flow. Further, since it is only necessary to previously derive two types of data, that is, the flow velocity Vn at the specified measuring point and the distance L within which the flow velocity is kept substantially equal to the issuing velocity Vn at the measuring point, the issuing flow-rate can be derived by using less number of data, making it possible to effect the measurement in a short period of time.

Figure 16:
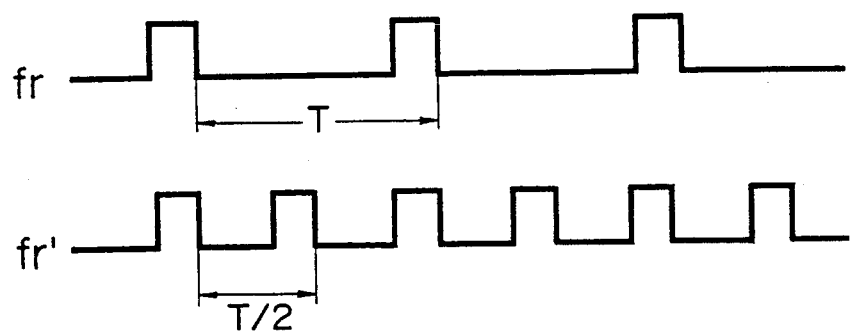
FIG. 16 is a waveform diagram showing rate pulses used in a modification of this invention.

This invention is not limited to the above embodiments and various modification can be made. For example, the flow velocity Vn which is limited by the sampling theorem can be set to be larger by setting the repetition frequency of the pulse for controlling the transmission/reception of the ultrasonic pulse to a frequency fr' which is twice the frequency fr generally used as shown in FIG. 16. As the result of this, a so-called aliasing of the blood flow can be alleviated so that a blood flow image which can be clearly observed can be obtained.

Figure 17:
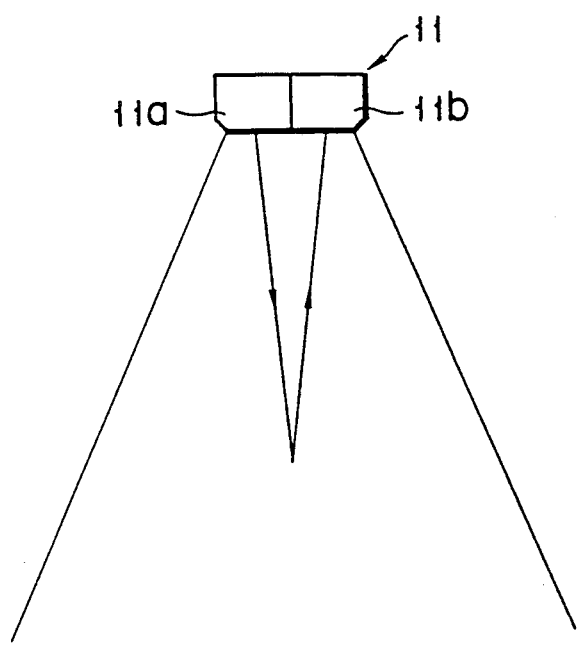
FIG. 17 is a view showing an ultrasonic probe of another modification of this invention.

Further, the measurement of the issuing flow-rate which is free from the influence by the aliasing can be attained by independently dispose a transmission probe 11a and a reception probe 11b as the ultrasonic probe 11 as shown in FIG. 17 and applying the continuous wave Doppler system. In this way, it becomes advantageous in the case of deriving high velocity blood flow information and the measurement precision of the issuing velocity can be enhanced.

Further, in the first and second embodiments, it is possible to use a plurality of second measuring points, derive a plurality of issuing flow-rates based on the velocity and the distance obtained for each point and derive the mean value of the issuing flow-rates to obtain a final issuing flow-rate. In this case, the measurement precision of the issuing flow-rate can be further enhanced.

In addition, this invention can be applied not only to the medical diagnosis in which the blood flow is treated but also to the other industrial field.

As described above, according to this invention, an ultrasonic Doppler apparatus can be provided which can derive the issuing flow-rate by use of the property of turbulent free jet without measuring the cross-sectional area.

What is claimed is:

1. An ultrasonic Doppler apparatus comprising:
    fluid imaging means for transmitting ultrasonic waves to a fluid issued from an orifice, receiving reflected echoes thereof, and displaying a tomographic image of the fluid and deriving a Doppler shift frequency of the fluid according to the received echoes;
    means for specifying a first point near the orifice on the tomographic image and a second point on a centerline of a portion of the issued fluid other than a laminar core of the issued fluid;
    first calculating means for deriving flow velocities at the first and second points based on the Doppler shift frequency derived by said fluid imaging means;
    second calculating means for deriving a distance between the first and second points; and
    third calculating means for deriving an issuing flow-rate of the fluid based on the flow velocities derived by said first calculating means and the distance derived by said second calculating means.

2. The apparatus according to claim 1, in which said third calculating means comprises means for deriving an issuing flow-rate Q according to the following equation:

$$Q = 0.017 \cdot Vx^2 \cdot M^2 / Vn$$

where Vn and Vx denote the flow velocities at the first and second points and M denotes the distance between the first and second points.

3. The apparatus according to claim 2, in which said first calculating means comprises means for deriving a flow velocity V according to the following equation:

$$V = fd \cdot C / (2fo \cdot \cos\theta)$$

where fd is the Doppler shift frequency, C is the velocity of the ultrasonic wave, fo is a center frequency of the ultrasonic waves, and θ is an angle between a propagation direction of the ultrasonic waves and the centerline of the issuing fluid.

4. The apparatus according to claim 1, in which said specifying means comprises means for specifying a plurality of second points, said first calculating means comprises means for deriving flow velocities at the plurality of second points, said second calculating means comprises means for deriving distances between the first point and the plurality of second points, and said third calculating means comprises means for deriving a plurality of issuing flow-rates based on the flow velocity at the first point, the flow velocities at the plurality of second points and the plurality of distances and means for deriving a mean value of the plurality of issuing flow-rates.

5. The apparatus according to claim 1, in which said fluid imaging means comprises:
    a plurality of piezoelectric transducers arranged in an array fashion, for transmitting the ultrasonic waves to the fluid and receiving the reflected echoes thereof;
    a mixer for multiplying output signals of said plurality of piezoelectric transducers by a signal of the center frequency of the transmitted ultrasonic waves;
    a low-pass filter for removing signal components of a frequency lower than twice the frequency of the center frequency from an output of said mixer;
    a moving target indicator filter for removing a clutter component from an output of said low-pass filter; and
    means for coloring the tomographic image according to the flow velocity and the moving direction of the fluid based on an output of said moving target indicator filter and for displaying the colored image.

6. An ultrasonic Doppler apparatus comprising:
    input means for specifying a given velocity;
    fluid imaging means for transmitting ultrasonic waves to a fluid issued from an orifice, receiving the reflected echoes thereof, and displaying a tomographic image of the fluid with a portion of the given velocity specified by said specifying means distinguished from the remaining portion on the tomographic image and deriving a Doppler shift frequency of the fluid according to the received echoes;
    means for specifying a first point near the orifice on the tomographic image and a second point on a centerline of the issued fluid within said distinguished portion of the given velocity;
    first calculating means for deriving a flow velocity at the first point based on the Doppler shift frequency derived by said fluid imaging means;
    second calculating means for deriving a distance between the first and second points; and
    third calculating means for deriving an issuing flow-rate of the fluid based on the given velocity, the flow velocity derived by said first calculating means and the distance derived by said second calculating means.

7. The apparatus according to claim 6, in which said third calculating means comprises means for deriving an issuing flow-rate Q according to the following equation:

$$Q = 0.017 \cdot Vx^2 \cdot M^2 / Vn$$

where Vn and Vx denote the flow velocities at the first and second points and M denotes the distance between the first and second points.

8. The apparatus according to claim 7, in which said first calculating means comprises means for deriving an flow velocity V according to the following equation:

$$V = fd \cdot C / (2fo \cdot \cos\theta)$$

where fd is the Doppler shift frequency, C is the velocity of the ultrasonic wave, fo is a center frequency of the ultrasonic waves, and $\theta$ is an angle between a propagation direction of the ultrasonic waves and the centerline of the issuing fluid.

9. The apparatus according to claim 6, in which said specifying means comprises means for specifying a plurality of second points, said first calculating means comprises means for deriving flow velocities at the plurality of second points, said second calculating means comprises means for deriving distances between the first point and the plurality of second points, and said third calculating means comprises means for deriving a plurality of issuing flow-rates based on the flow velocity at the first point, the flow velocities at the plurality of second points and the plurality of distances and means for deriving a mean value of the plurality of issuing flow-rates.

10. The apparatus according to claim 6, in which said fluid imaging means comprises:
   a plurality of piezoelectric transducers arranged in an array fashion, for transmitting the ultrasonic waves to the fluid and receiving the reflected echoes thereof;
   a mixer for multiplying output signals of said plurality of piezoelectric transducers by a signal of the center frequency of the transmitted ultrasonic waves;
   a low-pass filter for removing signal components of a frequency lower than twice the frequency of the center frequency from an output of said mixer;
   a moving target indicator filter for removing a clutter component from an output of said low-pass filter; and
   means for coloring the tomographic image according to the flow velocity and the moving direction of the fluid based on an output of said moving target indicator filter and for displaying the colored image.

11. An ultrasonic Doppler apparatus comprising:
   fluid imaging means for transmitting ultrasonic waves to a fluid issued from an orifice, receiving reflected echoes thereof, and displaying a tomographic image of the fluid and deriving a Doppler shift frequency of the fluid according to the received echoes;
   means for specifying a first point near the orifice on the tomographic image;
   first calculating means for deriving a flow velocity at the first point based on the Doppler shift frequency derived by said fluid imaging means;
   second calculating means for deriving a distance between said orifice and the front end of a laminar core of the issued fluid; and
   third calculating means for deriving an issuing flow-rate of the fluid based on the flow velocity derived by said first calculating means and the distance derived by said second calculating means.

12. The apparatus according to claim 11, in which said third calculating means comprises means for deriving an issuing flow-rate Q according to the following equation:

$$Q = 0.017 \cdot L^2 \cdot Vn$$

where Vn denotes the flow velocity at the orifice and L denotes said distance.

13. The apparatus according to claim 11, in which said fluid imaging means comprises means for displaying the tomographic image such that a portion of the image corresponding to a velocity substantially equal to the flow velocity at said orifice is distinguished from the remaining portion of the image, and said second calculating means comprises means for specifying a second point on the centerline of the issued fluid within said distinguished portion and means for deriving a distance between the first and second points.

14. The apparatus according to claim 11, in which said specifying means comprises means for specifying a plurality of second points, said first calculating means comprises means for deriving flow velocities at the plurality of second points, said second calculating means comprises means for deriving distances between the first point and the plurality of second points, and said third calculating means comprises means for deriving a plurality of issuing flow-rates based on the flow velocity a the first point, the flow velocities at the plurality of second points and the plurality of distances and means for deriving a mean value of the plurality of issuing flow-rates.

15. The apparatus according to claim 11, in which said fluid imaging means comprises:
   a plurality of piezoelectric transducers arranged in an array fashion, for transmitting the ultrasonic waves to the fluid and receiving the reflected echoes thereof;
   a mixer for multiplying output signals of said plurality of piezoelectric transducers by a signal of the center frequency of the transmitted ultrasonic waves;
   a low-pass filter for removing signal components of a frequency lower than twice the frequency of the center frequency from an output of said mixer;
   a moving target indicator filter for removing a clutter component from an output of said low-pass filter; and
   means for coloring the tomographic image according to the flow velocity and the moving direction of the fluid based on an output of said moving target indicator filter and for displaying the colored image.

* * * * *

UNITED STATES PATENT AND TRADEMARK OFFICE
CERTIFICATE OF CORRECTION

PATENT NO. : 5,062,427

DATED : November 05, 1991

INVENTOR(S) : Yasutsugu Seo et al.

It is certified that error appears in the above-identified patent and that said Letters Patent is hereby corrected as shown below:

Title Page, Foreign Application Priority Data, Delete "May 6, 1988 [JP] Japan......63-110171.

Abstract, line 8, before "Doppler" change "an" to --a--.

Abstract, line 22, before "display" change "an" to --a--.

Claim 3, column 12, line 9, change "8" to --θ--.

Claim 8, column 13, line 14, after "deriving" change "an" to --a--.

UNITED STATES PATENT AND TRADEMARK OFFICE
CERTIFICATE OF CORRECTION

PATENT NO.   : 5,062,427

DATED        : November 05, 1991

INVENTOR(S)  : Yasutsugu Seo et al.

It is certified that error appears in the above-identified patent and that said Letters Patent is hereby corrected as shown below:

Claim 14, column 14, line 41, after "velocity" change "a" to -- at --.

Signed and Sealed this

Twentieth Day of July, 1993

*Attest:*

MICHAEL K. KIRK

*Attesting Officer*     Acting Commissioner of Patents and Trademarks